US006680343B1

(12) United States Patent
Angello

(10) Patent No.: US 6,680,343 B1
(45) Date of Patent: Jan. 20, 2004

(54) TREATMENT OF RENAL COLIC WITH GABA ANALOGS

(75) Inventor: James T. Angello, Belle Mead, NJ (US)

(73) Assignee: Warner-Lambert Comapny, Morris Plains, NJ (US)

(*) Notice: Subject to any disclaimer, the term of this patent is extended or adjusted under 35 U.S.C. 154(b) by 0 days.

(21) Appl. No.: 09/720,007

(22) PCT Filed: Jul. 8, 1999

(86) PCT No.: PCT/US99/15387
§ 371 (c)(1),
(2), (4) Date: Dec. 19, 2000

(87) PCT Pub. No.: WO00/02547
PCT Pub. Date: Jan. 20, 2000

Related U.S. Application Data

(60) Provisional application No. 60/092,167, filed on Jul. 9, 1998.

(51) Int. Cl.$^7$ ............................................. A61K 31/195
(52) U.S. Cl. ........................................................ 514/561
(58) Field of Search .......................................... 514/561

(56) References Cited

FOREIGN PATENT DOCUMENTS

WO        98 03167        1/1998

OTHER PUBLICATIONS

Stedman's Medical Dictionary; 12$^{th}$ Edition, 1961; pp. 732 & 1031.*
Field, MJ, et al., "Gabapentin (Neurontin) and S–(+)–3–Isobutylgaba Represent a Novel Class of Selective Antihyperalgesic Agents", British Journal of Pharmacology, 1997, vol. 121:8, PP 1513–1522, XP002043785.
Wetzel, CH, et al., "Use of Gabapentin in Pain Management", Annals of Pharmacotherapy, 1997, vol. 31:9, PP 1082–1083, XP002101739.
PCT International Search Report (PCT/US99/15387) Mar. 20, 2000).

* cited by examiner

Primary Examiner—Raymond Henley, III
(74) Attorney, Agent, or Firm—Charles W. Ashbrook; James Proscia; Karen DeBenedictia

(57) ABSTRACT

The instant invention is a method of using certain analogs of glutamic acid and gamma-aminobutyric acid to relieve the pain associated with renal colic.

9 Claims, No Drawings

TREATMENT OF RENAL COLIC WITH GABA ANALOGS

This is a 371 of PCT/US99/15387 filed Jul. 8, 1999 which claims benefit to U.S. Provisional Application No. 60/092,167 filed Jul. 9, 1998.

BACKGROUND OF THE INVENTION

1. Field of the Invention

The present invention relates to the use of analogs of glutamic acid and gamma-aminobutyric acid (GABA) for treatment of renal colic.

2. Description of Related Art

GABA analogs are known agents useful in antiseizure therapy for central nervous system disorders such as epilepsy, Huntington's chorea, cerebral ischemia, Parkinson's disease, tardive dyskinesia, and spasticity. It has also been suggested that the compounds can be used as antidepressants, anxiolytics and antipsychotics. See WO 92/09560 (U.S. Ser. No. 618,692 filed Nov. 27, 1990) and WP 93/23383 (U.S. Ser. No. 886,080 filed May 20, 1992).

WO 97/33858 teaches that compounds related to gabapentin are useful for treating epilespy, faintness attacks, hypokinesia, cranial disorders, neurodegenerative disorders, depression, anxiety, panic, pain, and neuropathological disorders. WO 97/33858 does not specify what forms of pain are treated.

Additionally, the compounds of the invention are known for treatment of neuropathic pain. For example, see Rosner H; Rubin L; Kestenbaum A., Gabapentin adjunctive therapy in neuropathic pain states. Clin J Pain, March 1996, 12:1, 56–8; Segal A Z; Rordorf G., Gabapentin as a novel treatment for postherpetic neuralgia. Neurology, April 1996, 46:4, 1175–6; Wetzel C H; Connelly J F., Use of gabapentin in pain management. Ann Pharmacother, September 1997, 31:9, 1082–3; Zapp J J., Postpoliomyelitis pain treated with gabapentin [letter]. Am Fam Physician, June 1996, 53:8, 2442, 2445; Cheville A, et al., Neuropathic pain in radiation myelopathy:a case report. Program book, American Pain Society (14th Annual Scientific Meeting). Abstract #95823, p. A-115; Sist T; Filadora V; Miner M; Lema M., Gabapentin for idiopathic trigeminal neuralgia: report of two cases. Neurology, May 1997, 48:5, 1467; Waldman S D, Tutorial 28: Evaluation and Treatment of Trigeminal Neuralgia. Pain Digest (1997) 7:21–24; Mellick L B; Mellick G A., Successful treatment of reflex sympathetic dystrophy with gabapentin [letter]. Am J Emerg Med, January 1995, 13:1, 96; Mellick G A; Seng M I., The use of gabapentin in the treatment of reflex sympathetic dystrophy and a phobic disorder. Am J Pain Manage 1995; 5:7–9; Mellick G A; Mellicy L B; Mellick L B., Gabapentin in the management of reflex sympathetic dystrophy [letter]. J Pain Symptom Manage, May 1995, 10:4, 265–6; Mellick G A; Mellick L B., Reflex sympathetic dystrophy treated with gabapentin. Arch Phys Med Rehabil, January 1997, 78:1, 98–105 and Mackin G A., Medical and pharmacologic management of upper extremity neuropathic pain syndromes. J Hand Ther, April–June 1997, 10:2, 96–109.

Renal colic is commonly known as kidney stones. The passage of these crystalline fragments is so painful that it is proverbially known as the male equivalent of "child birth or labor." Patients are in such agony, that they are often rushed to hospital emergency rooms for treatment. While not life-threatening, the pain is so incapacitating that patients are often started on narcotic pain relievers.

The typical renal colic sufferer makes an initial visit to the hospital and is given i.m. morphine or equivalent for about 48 hours after diagnosis. Then the patient is sent home on oral narcotic analgesics and ESWL (lithotripsy) is performed within 1 week. Typically all of the fragments pass at home within two weeks. The pain intensity is universally on the top of all pain scales.

According to Urinary Calculi: ESWL, Endourology, and Medical Therapy, James E. Lingeman, et.al., 1994:51–71, the incidence of kidney stones is 335,000 patients/year (ie, those who are admitted to the ER because of renal colic). According to the Merck Manual, approximately 1 in every 1000 adults is hospitalized annually in the USA because of urinary stones (which equals about 200,000 per year).

About 80% of urinary calculi, or kidney stones, are composed of Ca, mainly calcium oxalate; 5% are uric acid; 2% cystine; and the remainder, magnesium ammonium phosphate. All of these stones are crystalline in structure, often with sharp edges that resemble small pieces of broken glass. Whether the stones pass through the ureter intact and spontaneously or in fragments following extracorporeal shock wave lithotripsy, extreme pain typically accompanies ureteral passage. This pain is often only partially relieved, even with the use of narcotic analgesics like morphine.

SUMMARY OF THE INVENTION

This invention provides a method for treating renal colic comprising administering to a subject suffering from such pain an effective amount of a GABA analog. A preferred embodiment utilizes a cyclic amino acid compound of Formula I

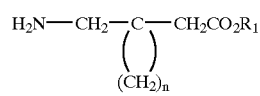

wherein $R_1$ is hydrogen or lower alkyl and n is an integer of from 4 to 6, and the pharmaceutically acceptable salts thereof. An especially preferred embodiment utilizes a compound of Formula I where $R_1$ is hydrogen and n is 4, which compound is 1-(aminomethyl)-cyclohexane acetic acid, known generically as gabapentin.

In another embodiment, the invention includes treating renal colic pain with a compound of Formula II.

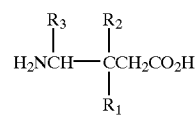

wherein $R_2$ is a straight or branched alkyl of from 1 to 6 carbon atoms, phenyl, or cycloalkyl having from 3 to 6 carbon atoms; $R_3$ is hydrogen or methyl; and $R_4$ is hydrogen, methyl, or carboxyl; or an individual enantiomeric isomer thereof; or a pharmaceutically acceptable salt thereof, in unit dosage form, to a mammal in need of said treatment.

Preferred compounds of the invention are those wherein $R_4$ and $R_3$ are hydrogen, and $R_2$ is $—(CH_2)_{0-2}-iC_4H_9$ as an (R), (S), or (R,S) isomer.

The more preferred compounds of Formula II invention are (S)-3-(aminomethyl)-5-methylhexanoic acid and 3-aminomethyl-5-methyl-hexanoic acid, now known generically as pregabalin.

DETAILED DESCRIPTION OF THE PREFERRED EMBODIMENTS

The method of this invention utilizes any GABA analog. A GABA analog is any compound derived from or based upon gamma-aminobutyric acid. The compounds are readily available, either commercially, or by synthetic methodology well-known to those skilled in the art of organic chemistry. The preferred GABA analogs to be utilized in the method of this invention are cyclic amino acids of Formula I. These are described in U.S. Pat. No. 4,024,175, which is incorporated herein by reference. Another preferred method utilizes the GABA analogs of Formula II, and these are described in U.S. Pat. No. 5,563,175 which is incorporated herein by reference.

All that is required to practice the method of this invention is to administer a GABA analog in an amount that is effective to treat pain associated with renal colic. Such anti-pain amount will generally be from about 1 to about 300 mg per kg of subject body weight. Typical doses will be from about 10 to about 5000 mg per day for an adult subject of normal weight. It is expected that common doses that might be administered for renal colic could be from 100 mg three times a day up to 600 mg four times a day. Commercially available capsules of 100 mg, 300 mg and 400 mg of gabapentin can be administered. Alternate forms include liquids and film-coated tablets.

If a compound of Formula II, such as pregabalin is used, the dosage level is one sixth that of gabapentin. The dosage range for pregabalin is from about 0.15 mg to about 50 mg per kg per day of subject body weight. Typical dosages for pregabalin will be from about 1.6 mg to about 840 mg per day with individual dosages ranging from abut 0.15 mg to about 65 mg per dose.

The compounds of the present invention may form pharmaceutically acceptable salts with both organic and inorganic acids or bases. For example, the acid addition salts of the basic compounds are prepared either by dissolving the free base in aqueous or aqueous alcohol solution or other suitable solvents containing the appropriate acid and isolating the salt by evaporating the solution. Examples of pharmaceutically acceptable salts are hydrochlorides, hydrobromides, hydrosulfates, etc. as well as sodium, potassium, and magnesium, etc. salts.

The compounds of the Formula II can contain one or several asymmetric carbon atoms. The invention includes the individual diastereomers or enantiomers, and the mixtures thereof. The individual diastereomers or enantiomers may be prepared or isolated by methods already well-known in the art.

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses.

Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol, glycerin; sorbitol; polyethylene glycol; water; agar; alginic acid; isotonic saline, and phosphate buffer solutions; as well as other compatible substances normally used in pharmaceutical formulations.

The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredients in the foregoing compositions can be varied within wide limits, but for practical purposes it is preferably present in a concentration of at least 10% in a solid composition and at least 2% in a primary liquid composition. The most satisfactory compositions are those in which a much higher proportion of the active ingredient is present.

Routes of administration of the subject compound or its salts are oral or parenteral. For example, a useful intravenous dose is between 5 and 50 mg and a useful oral dosage is between 20 and 800 mg. The dosage is within the dosing range used in treatment of pain or as would be with the needs of the patient as described by the physician.

A unit dosage form of the GABA analog to be used in this invention may also comprise other compounds useful in the treatment of pain. These could include the urinary analgesic, phenazopyridine, as well as systemic analgesics.

The advantages of using the compounds of Formula I and II, especially gabapentin and pregabalin, in the instant invention include the relatively nontoxic nature of the compounds, the ease of preparation, the fact that the compounds are well-tolerated, and the ease of IV administration of the drugs. Gabapentin has few interactions with major classes of drugs since it is not metabolized in the liver, but rather excreted unchanged from the body. Further, the drugs are not metabolized in the body. The subjects treated with the method of the present invention are mammals, including humans.

While not wishing to be bound by any theory, the present invention appears to work because GABA analogs have been proposed to work both peripherally and centrally to relieve pain and to interact with a specific receptor in calcium channels. This calcium channel interaction is of particular interest when considering its potential role in renal colic, since calcium channel antagonists such as nifedipine have been shown to relieve the pain and promote passage of renal calculi through a vasodilatory effect on the ureter smooth muscle. This action of GABA analogs, specifically gabapentin, is confirmed, in part, by a documented low incidence of peripheral edema and vasodilatation. Thus, gabapentin could have a dual mechanism in the relief of acute renal colic through its interference with central and peripheral pain pathways in addition to its potential to provide ureter smooth muscle relaxation. Based on this possible dual mechanism gabapentin provides superior pain relief for renal colic relative to existing analgesics.

What is claimed is:

1. A method for treating a mammal suffering from renal colic comprising administering to said mammal a pharmaceutical composition comprising an effective amount of a GABA analog.

2. The method according to claim 1, wherein the GABA analog is the compound according to Formula I:

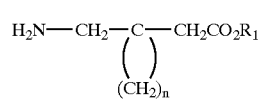

wherein $R_1$ is hydrogen or lower alkyl and n is an integer of from 4 to 6, and the pharmaceutically acceptable salts thereof.

3. The method according to claim 2, wherein Formula I comprises gabapentin.

4. The method according to claim 2, comprising from about 10 mg to about 400 mg of Formula I.

5. The method according to claim 3, comprising from about 10 mg to about 400 mg of gabapentin.

6. The method according to claim 1, wherein the GABA analog is a compound according to Formula II:

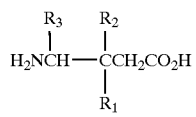

II or a pharmaceutically acceptable salt thereof wherein
- $R_1$ is a straight or branched alkyl of from 1 to 6 carbon atoms, phenyl, or cycloalkyl of from 3 to 6 carbon atoms;
- $R_2$ is hydrogen or methyl; and
- $R_3$ is hydrogen, methyl, or carboxyl.

7. The method according to claim 6, wherein Formula II comprises pregabalin.

8. The method according to claim 6, comprising administering from about 0.15 mg to about 65 mg per kg of a compound of Formula II.

9. The method according to claim 7, comprising administering from about 0.15 mg to about 65 mg per kg of a compound of pregabalin.

* * * * *